United States Patent [19]

Cicchetti

[11] Patent Number: 6,102,697
[45] Date of Patent: Aug. 15, 2000

[54] HOLDING DEVICE FOR MANUFACTURE OF DENTAL BRIDGES AND MANUFACTURING PROCESS FOR MANUFACTURE OF DENTAL BRIDGES

[76] Inventor: Biagio Cicchetti, P.za Degli Olmi, I-75100 Matera, Italy

[21] Appl. No.: 09/101,111

[22] PCT Filed: Jan. 20, 1997

[86] PCT No.: PCT/EP97/00253

§ 371 Date: Oct. 2, 1998

§ 102(e) Date: Oct. 2, 1998

[87] PCT Pub. No.: WO97/25934

PCT Pub. Date: Jul. 24, 1997

[30] Foreign Application Priority Data

Jan. 19, 1996 [DE] Germany ............................ 196 01 894

[51] Int. Cl.⁷ ............................ A61C 13/00; A61C 14/00
[52] U.S. Cl. ............................................. 433/49; 433/223
[58] Field of Search ............................... 433/49, 50, 53, 433/141, 223

[56] References Cited

U.S. PATENT DOCUMENTS

| | | | |
|---|---|---|---|
| 3,277,576 | 10/1966 | Kraft | 433/53 |
| 4,952,151 | 8/1990 | Metcalfe | 433/53 |
| 5,028,235 | 7/1991 | Smith | 433/223 |
| 5,135,393 | 8/1992 | Eidenbenz et al. | 433/50 |

FOREIGN PATENT DOCUMENTS

| | | | |
|---|---|---|---|
| 3201397 | 12/1982 | Germany | 433/49 |
| 3719039 | 12/1988 | Germany | 433/213 |
| 3914623 | 11/1990 | Germany | 433/49 |
| 88/10101 | 12/1988 | WIPO | 433/213 |

*Primary Examiner*—Ralph A. Lewis
*Attorney, Agent, or Firm*—Anthony J. Casella; Gerald E. Hespos; Michael J. Porco

[57] ABSTRACT

The present invention relates to a holding device for the manufacture of dental bridges or for connecting adjacent tooth crowns or onlays/inlays, which device comprises: a main part (10; 110) and at least two support arms (20-1, 20-2, 20-3; 120-1 to 120-6) which extend from the main part (10; 110), each support arm (20-1, 20-2, 20-3; 120-1 to 120-6) comprising at least one support element (30-1, 30-2, 30-3; 130-1 to 130-6) which extends from the support arm (20-1, 20-2, 20-3; 120-1 to 120-6) at a predetermined or predeterminable angle. The invention further relates to a manufacturing process for manufacturing dental bridges.

22 Claims, 3 Drawing Sheets

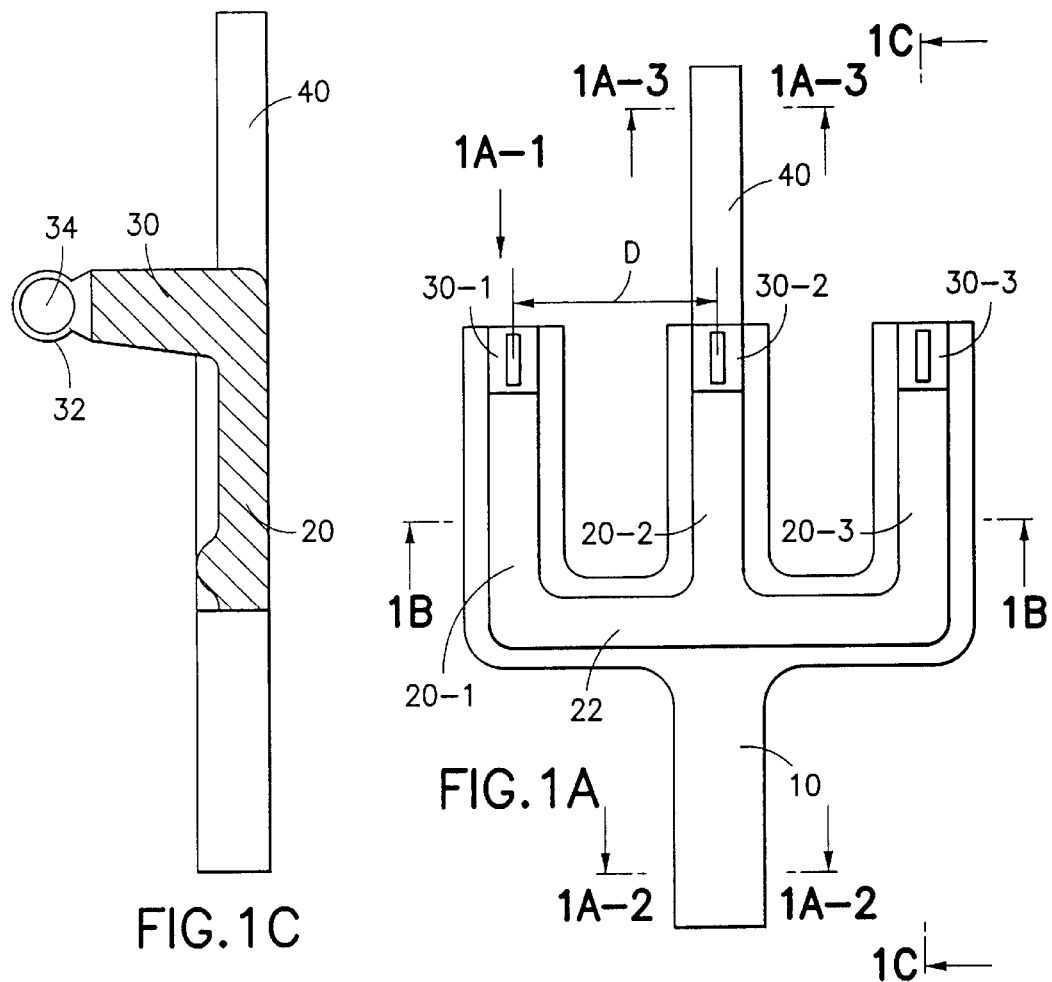
FIG. 1A
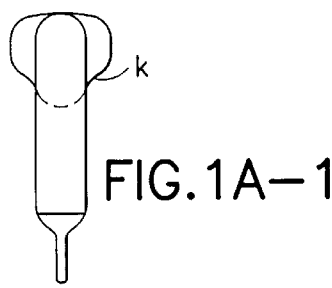
FIG. 1A-1
FIG. 1A-2
FIG. 1A-3
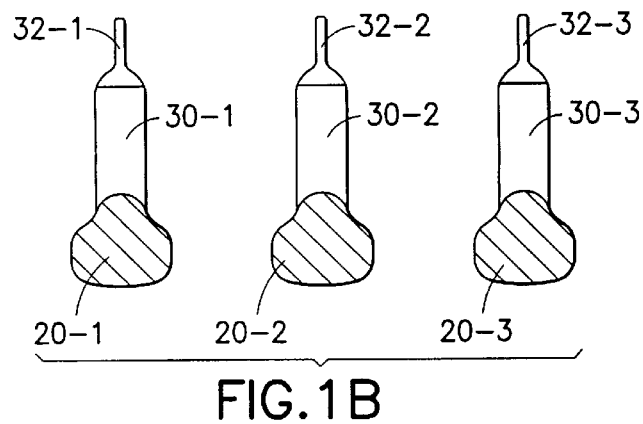
FIG. 1B
FIG. 1C

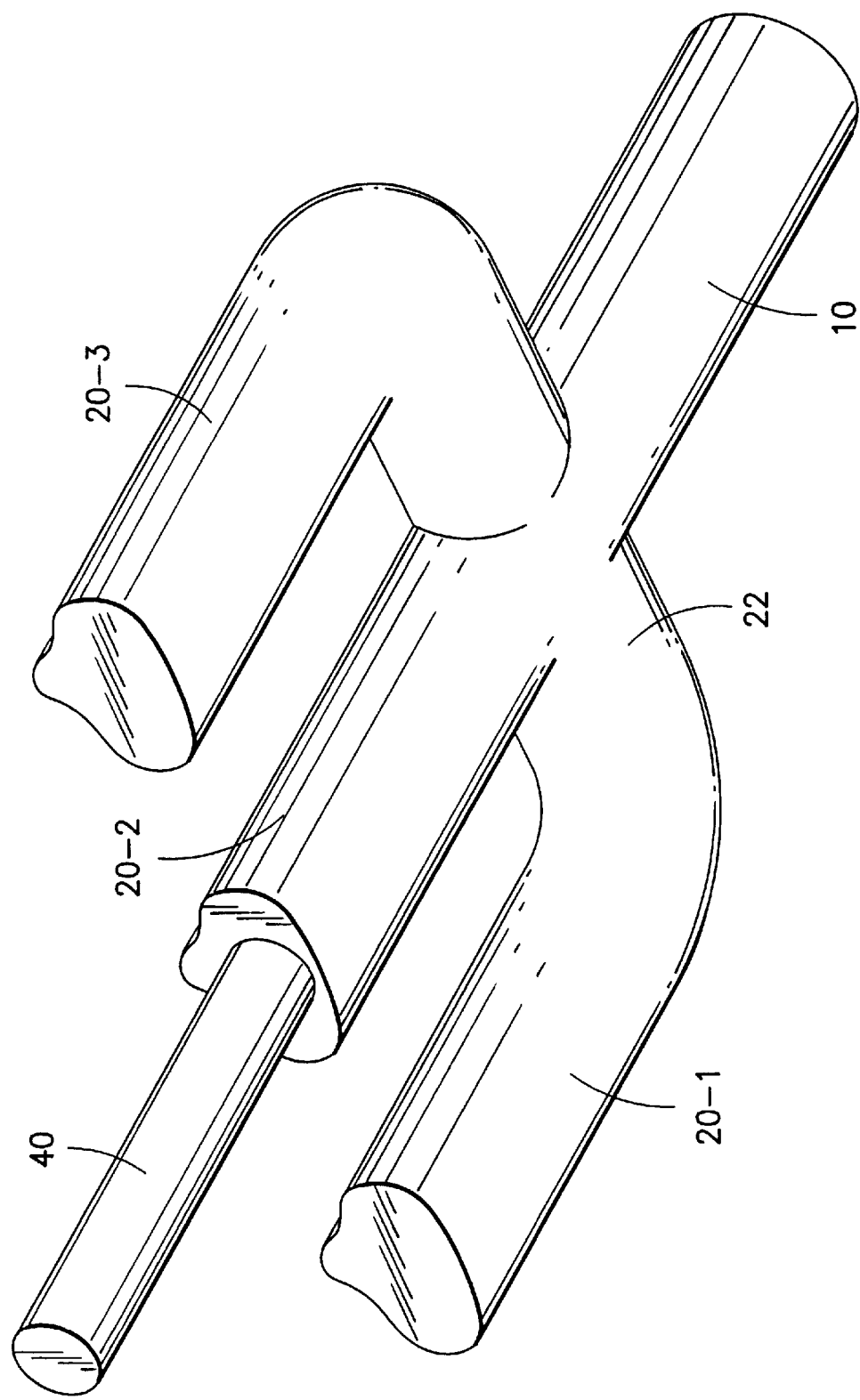

HOLDING DEVICE FOR MANUFACTURE OF DENTAL BRIDGES AND MANUFACTURING PROCESS FOR MANUFACTURE OF DENTAL BRIDGES

DESCRIPTION

The present invention relates to a holding device for the manufacture of dental bridges or for connecting adjacent tooth crowns or onlays/inlays, the use thereof for the manufacture of dental bridges and/or for connecting adjacent tooth crowns or onlays/inlays, and a manufacturing process for the manufacture of dental bridges and of connected tooth crowns.

It is known to span tooth gaps, in particular tooth gaps existing between two teeth, by means of a tooth replacement, the so-called dental bridges, which are supported by the residual dentition.

It is also known to manufacture the dental bridges as follows:

A. Negative impressions are taken of the individual bridge abutments, i.e. of the prepared and in particular essentially frustoconically ground teeth. This is done in particular using a silicone-type material or liquid (e.g. CAPSIL® from Leach & Dillon, Attleboro Mass. 02763 USA). The negative impressions can here be taken directly on the patient or on a plaster model, prepared by the dentist, of the relevant tooth section of the patient.

B. A positive impression of the individual bridge abutments of the negative impression is made using a refractory material. To do this, a composition or liquid capable of solidifying (e.g. CAPVEST® from Leach & Dillon) is filled into the negative impression, cured and subjected to thermal cycles in order to sinter the composition, e.g. by heating at 700° C. for 10 minutes and then at 1075° C. for 4 minutes.

The refractory material can be formed from a phosphate-bound embedding compound. The phosphate-bound embedding compound contains in the powder of metal oxide, mostly magnesium oxide, phosphates such as ammonium dihydrogen phosphate ($NH_4H_2PO_4$) and expanding quartz modifications. On admission of water, both hydrogen atoms are replaced by the magnesium and the salt of phosphoric acid arises. Upon crystallization, this salt takes up $6H_2O$ as water of crystallization. At 200°–250° C., the water of crystallization escapes, and at about 300° C. the $NH_4MgPO_4$ loses ammonia ($NH_3$). This therefore results in red-heat-stable and binding magnesium pyrophosphate ($Mg_2P_2O_7$).

C. Application of a substance (e.g. "CAPTEK® adesivo" from Leach & Dillon) onto the refractory material in order to facilitate the subsequent application of the alloy for the crowns.

D. Application of a base structure for the crowns onto the specially treated, refractory material. The base structure can in particular comprise an Au-Pt-Pd-Ag alloy (e.g. CAPTEK P® from Leach & Dillon) which, under the microscope, is seen in the form of differently sized splinters which are bound in particular by a silicone-type material used in the electronics industry. The alloy can be formed in laminas which can have different thicknesses depending on the area of application (e.g. 0.25 mm for front teeth and 0.35 mm for back teeth such as molars and premolars). Upon application, it is ensured that the base structure lies in close contact on the specially treated, refractory material. The shape of the base structure can be stabilized by thermal cycling, e.g. at 1075° C. for 4 minutes. However, there must not yet be complete melting or fusion of the base structure, and instead the splinters can be melted on so that the base structure can be porous.

E. A capillarization material or agent is then applied. This capillarization material (e.g. CAPTEK G® from Leach & Dillon) comprises in particular an Au-based alloy with hard or hardener metals, or metals for hardening the alloy, which are seen under the microscope in the form of differently sized spheres, in particular after the binder has been removed and the agent atomized (and by melting in an atmosphere of inert gas, e.g. Ar and by spraying). The capillarization material can be formed in laminas, which can have different thicknesses depending on the area of application. The capillarization material is intended to fill or saturate the free spaces of the base structure. The capillarization material forms a surface layer which on average is in particular about 5 $\mu$m, but depending on the application can also be up to 100 $\mu$m. The capillarization procedure can also include thermal cycling.

The amount of capillarization material is advantageously chosen about equal to the amount of base structure material in order to achieve good capillarization.

F. Mechanical separation of the crown from the refractory material and removal of residues of the refractory material by scraping and/or rubbing and/or by using HCl, e.g. with a 20% dilution.

G. The crowns are then fitted, in particular by milling, on the positive "master impression", e.g. of plaster, which was taken from the bridge abutments, in order to improve the seat or fit of the crowns on the bridge abutments.

The bridge is now formed between the bridge abutments provided with crowns.

F. An intermediate element or intermediate member is chosen whose bridge body, bridge anchors (connection elements of the intermediate element) and size are suitable for the application. The intermediate element can comprise a Pd-based alloy with two percent Au.

G. Fitting the intermediate element in the space of the missing tooth, the bridge anchors being fitted in particular to the crowns.

H. Securing the intermediate element on the crowns by means of an adhesive material, e.g. wax.

I. Producing a further positive cast of refractory material in which the relative positions of the bridge abutments, i.e. of the prepared teeth, are reproduced. The refractory material is in particular free from ammonium sulfate.

J. Transferring the connected crowns and intermediate element to the further positive cast in order to fix the relative positions of the crowns and of the intermediate element during their final connection (e.g. by welding and/or by connection materials).

K. Removing the adhesive material, e.g. by washing.

L. Connecting the crowns and the intermediate element to one another, e.g. by means of a connection material (e.g. CAPCON® from Leach & Dillon) which has a similar composition to the material for the base structure (e.g. CAPTEK P® from Leach & Dillon). The connection material can also comprise an antioxidizing flux agent which prevents oxidation of the connection material when it is being heated.

M. Filling the bridge with a filler material. The filler material (e.g. CAPFIL® from Leach & Dillon) can include a gold alloy which has a similar composition to the capillarization material (e.g. CAPTEK G®) and a melting point of about 1075° C.

N. Final welding of the intermediate element with the crowns in order to produce the bridge. The welding is done, for example, by thermal cycling similar to the previous steps.

O. Removing the bridge from the refractory material, checking it on the master cast and applying an outermost ceramic layer.

It is also known (B. Romano et al, "Società Lucana di medicina e chirurgia", Atti 1989–1990, pages 389–398) to use a material with trade names CEPLATEC® or CEPLATEC Crown Bridge Systems® (trade name in Europe, in particular in Italy) or Renaissance® (trade name in USA and Japan).

However, these known manufacturing processes for bridges have the disadvantage that because of the large number of steps, they require about four hours. In the first process, the further positive cast of refractory material, which is produced in step 1 and in which the relative positions of the bridge abutments (i.e. of the prepared teeth) are reproduced, is also exposed to considerable thermal dilations and expansions during welding, which dilations and expansions impair the accuracy of the final bridge. In addition, each manufacturing step is subject to inaccuracies and possible errors, so that the manufactured bridge may be defective.

The object of the present invention is therefore to make available a holding device for the manufacture of dental bridges or for connecting adjacent tooth crowns or onlays/inlays, the use thereof for the manufacture of dental bridges and/or for connecting adjacent tooth crowns or onlays/inlays, and a manufacturing process for the manufacture of dental bridges and of connected tooth crowns, which holding device permits fast and accurate manufacture of the bridges or of the connection of adjacent crowns.

According to the invention, this object is achieved by a holding device as claimed in claim 1, its use as claimed in claim 19, and by a manufacturing process as claimed in claim 20 or 26. Preferred embodiments of the present invention are the subject matter of the subclaims.

According to the invention, a holding device for the manufacture of dental bridges or for connecting adjacent tooth crowns or onlays/inlays comprises a main part and at least two support arms which extend from the main part, each support arm comprising at least one support element which extends from the support arm at a predetermined or predeterminable angle from the surface defined by the support arm.

The holding device according to the invention thus avoids the problem of thermal expansions of the refractory materials when forming the connections, e.g. welds or solders, and indeed this applies to both primary hard soldering (at temperatures of about 1040° to 1120° C.) and secondary hard soldering (at temperatures of about 750° to 850° C.)

Thus, considerable thermal dilations are largely avoided particularly during welding, and it is no longer necessary to separate the individual casts from bridge abutments in order to avoid thermal dilations, and to make a further cast in which the relative positions of the bridge abutments are reproduced, since the holder according to the invention on the one hand greatly reduces thermal dilations of the refractory material, as the overall mass of the refractory material is reduced, and the relative positions are fixed by the holder.

According to a preferred embodiment of the invention, the support arms have, at least adjacent to the support elements, essentially a cross section whose limiting curve deviates from a circle, the limiting curve of the cross section preferably having a bulb shape or rounded T shape or "pear shape" or corresponds to a rounded superposition of two ellipses directed essentially perpendicular to one another, and in particular has at least two points of reversal of curvature.

This embodiment prevents the occurrence of hairline cracks or stresses via corners or edges on the support elements in the refractory material, as a result of which the accuracy of the positioning of the cast and the good reproduction of the impression or cast pattern are ensured. In addition, good rigidity is ensured by means of the bulb shape or the rounded T shape, as a result of which the support elements do not move, e.g. during welding of the intermediate element to the crowns, and ensure a good working accuracy.

The support elements preferably taper away from the support arms, i.e. their cross-sectional area decreases, in which case the support elements are preferably of an essentially frustoconical design. It is thus advantageously possible to remove the refractory material or cast from the individual support element, e.g. for further adaptation or other use.

In addition, the support elements can preferably each comprise at least one retention arrangement, the retention arrangement preferably having a through-bore and being in particular of circular design, or the retention arrangement preferably being of spherical design.

The retention arrangement thus advantageously prevents the refractory material coming loose from the support elements.

According to a further embodiment, the support arms run essentially parallel to one another or are arranged at an angle, in particular perpendicular, to a connection element which is in particular arched and which connects the support arms, and the arched connection element corresponds at least partially and approximately to the arched arrangement of teeth in the jaw. This thus permits an advantageous adaptation to the negative impression or cast, in particular to the arrangement of the teeth.

The connection element is preferably designed in one piece with the support arms. This permits a simple and robust construction.

Two adjacent support elements are particularly preferably spaced apart by a distance which is in the range from about 6 to about 12 mm, preferably from about 8 to 10 mm, and most preferably about 9 mm, and in particular according to the average distance between adjacent teeth.

A bearing projection is also preferably formed on one or more support arms. This ensures stabilization of the holding device, particularly during the pouring of a filling composition into the interspace between negative impression and the support elements.

The holding device is particularly preferably made of a material, in particular a metal or an alloy, whose melting point lies above about 1100° C., preferably above about 1150° C., most preferably above about 1200° C., and/or which has a low coefficient of thermal expansion. Thus, the holding device is not damaged during welding and it permits a good relative positioning of the crowns and the intermediate element.

In addition, the support arms preferably extend by a length which is in the range from about 10 to 30 mm, preferably from about 12 to 20 mm, particularly preferably from about 14 to about 16 mm, as measured from about the center of the support element to about the center of the connection element. A good stability and a low thermal expansion are thus ensured.

The support arms are particularly preferably designed in one piece, each support arm being preferably designed in one piece with the corresponding support element. This permits a simple and stable construction.

The invention also concerns the use of the holding device according to the invention for the manufacture of dental bridges and/or for connecting adjacent tooth crowns or onlays/inlays, in particular for supporting adjacent teeth on one another.

The use of the holding device according to the invention is possible both for the above-described CAPTEK® technique, and also for the techniques which use OPTEK®, CEPLATEC® and CEPLATEC Crown Bridge System® (trade name in Europe, in particular in Italy) or Renaissance® (trade name in USA and Japan).

The invention can also be used in particular for free-end bridges and continuous bridges.

The invention also makes available a manufacturing process for the manufacture of dental bridges, which process comprises the following steps:

a) forming a negative impression of a partial area of the dentition or residual dentition;

b) arranging at least two support elements of a holding device according to the invention in the sections, in particular the cavities, of the negative impression corresponding to the teeth or tooth gaps;

c) filling interspaces between the negative impression and the support elements with a filler material consisting of a material which is capable of solidifying, and which in the solidified state is refractory, in particular with a phosphate-bound embedding compound (e.g. CAPVEST®), in order to form a positive impression of the partial area of the dentition;

d) curing the filler material;

e) removing the support elements and the filler material connected thereto, i.e. the positive impression, from the negative impression;

f) fitting an intermediate element or intermediate member, to be used for the bridge, onto bridge abutments of the positive impression;

g) securing the intermediate element on the positive impression of an edentulous saddle or seat ("sella edentula" in Italian) between the bridge abutments, in particular on a plaster impression of the partial area of the dentition, e.g. the master impression made of plaster;

h) forming base layers of the crowns on the positive impressions of the bridge abutments, in particular with a base structure made up of a gold alloy (e.g. CAPTEK P®);

i) forming the crowns on the impressions of the bridge abutments, in particular with the intermediate element removed (e.g. by means of CAPCON®, CAPTEK G®, CAPFIL®);

j) arranging the intermediate element once again between the crown-fitted positive impressions of the bridge abutments;

k) connecting the intermediate element to the crowns (e.g. by means of CAPTEK G®, CAPCON®, CAPFIL®);

l) completing the crowns and the bridge, in particular by a ceramic coating.

The manufacturing process according to the invention advantageously comprises a small number of steps for manufacturing the bridge, as a result of which the time needed for manufacture is reduced to about two hours, corresponding to half the time for the conventional manufacturing process, by which means the manufacturing costs are appreciably reduced. In particular, the conventional steps of securing the intermediate element by means of wax (step H) and manufacturing a further positive impression and transferring the bridge blank to the further cast (step J) are eliminated by the manufacturing process according to the invention.

Moreover, the smaller number of necessary steps also brings with it a reduction in the possible errors, as a result of which the amount of rejected material is advantageously reduced. The manufacturing process according to the invention moreover permits a higher manufacturing accuracy.

According to a preferred embodiment, the manufacturing process comprises, after removal step e):

e') applying and/or curing a silicone-type material onto the refractory filler composition (e.g. CAPTEK® adesivo) and/or e") securing a wax layer corresponding to a thickness of the final crown which is to be formed, in particular on a plaster impression of the partial area of the dentition.

The securing step g) is preferably carried out using a hard wax. The manufacturing process also preferably comprises, after step h) in which a base layer is formed:

h') forming receivers for connection elements or bridge anchors of the intermediate element which connects an intermediate element body to the bridge abutment, the receivers at least partially supporting the connection elements from underneath and/or at the sides.

Step k) involving connection of the intermediate element is also preferably carried out using a gold alloy for capillarizing, i.e. for saturating or filling the voids, in particular by thermal cycling.

The manufacturing process also preferably comprises, after step k) involving connection of the intermediate element:

k') improving or repairing the sealing edges of the crowns.

The invention also makes available a manufacturing process for the manufacture of connected tooth crowns or onlays/inlays, which process comprises the following steps:

a) forming a negative impression of a partial area of the dentition or residual dentition;

b) arranging at least two support elements of a holding device according to the invention in the sections, in particular cavities, of the negative impression corresponding to the teeth or tooth gaps;

c) filling interspaces between the negative impression and the support elements with a filler material consisting of a material which is capable of solidifying, and which in the solidified state is refractory, in particular with a phosphate-bound embedding compound (e.g. CAPVEST®), in order to form a positive impression of the partial area of the dentition;

d) curing the filler material;

e) removing the support elements and the filler material connected thereto, i.e. the positive impression, from the negative impression;

f) forming base layers of the crowns on the positive impressions of the bridge abutments, in particular with a base structure made up of a gold alloy (e.g. CAPTEK P®);

g) forming the crowns on the impressions of the bridge abutments (e.g. by means of CAPCON®, CAPTEK G®, CAPFIL®);

h) connecting the crown, in particular by welding (e.g. by means of CAPTEK G®, CAPCON®, CAPFIL®);

i) completing the crowns and the bridge, in particular by a ceramic coating.

According to a preferred embodiment of the present invention, the curing step d) comprises a step for removing ammonia from the filler material.

Further features and advantages of the present invention will become evident from the following illustrative description of preferred embodiments, with reference being made to the attached drawing, in which:

FIG. 1(A) is a plan view of a first embodiment of the holding device according to the invention;

FIG. 1(B) is a sectional view along the line A—A in FIG. 1(A);

FIG. 1(C) is a sectional view along the line B—B in FIG. 1(A);

FIG. 2 is a perspective view of the embodiment shown in FIG. 1, but with the support elements not shown.

Figure 3A:
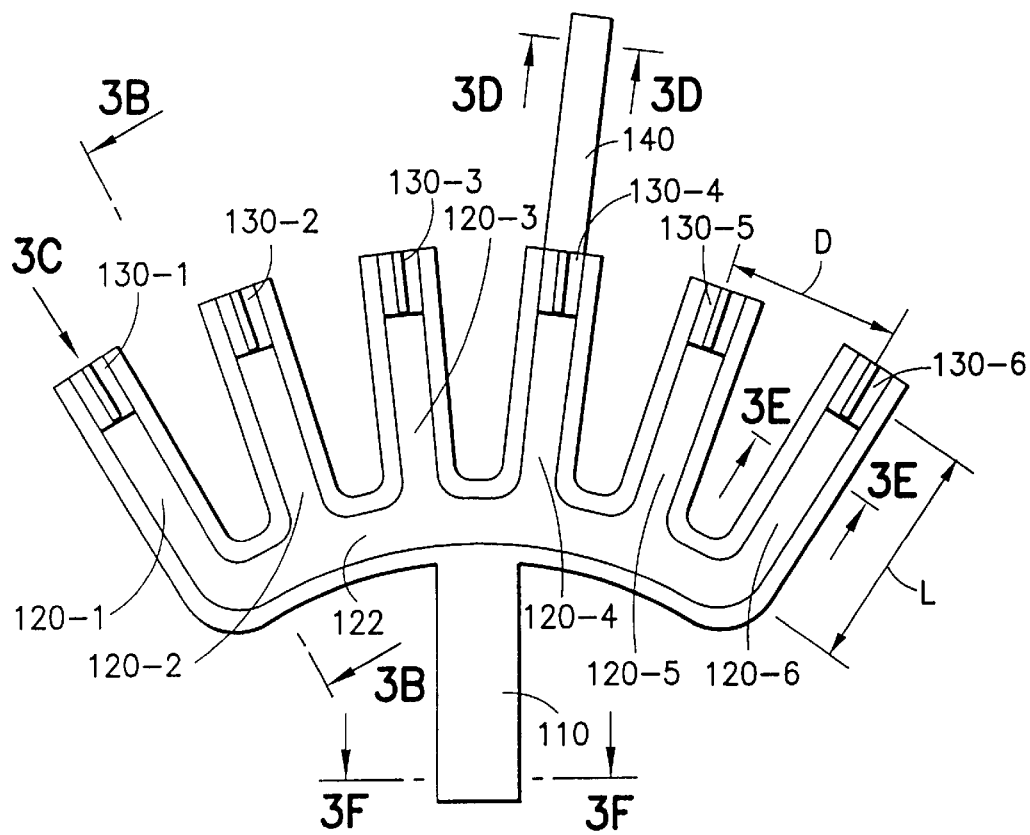
FIG. 3 is a plan view of a second embodiment of the present invention.

The first embodiment of the holding device according to the invention, as shown in FIGS. 1 and 2, comprises a main part 10, on which three support arms 20-1, 20-2, 20-3 are secured, the holding device having in particular the shape of a rake or three-pronged fork. The support arms 20-1, 20-2, 20-3 run parallel to one another and are connected to one another via a connection element 22, the support arms 20 each being arranged approximately perpendicular to the longitudinal axis of the connection element 22.

The support arms 20 and the connection element 22 have a "pear-shaped" or bulb-shaped cross section which is represented by the curve K in FIG. 1(A). The cross section deviates from a circular cross section and yet has no edges or corners, as a result of which cracks and stresses in a refractory or heat-resistant or nonmeltable material ("materiale refrattario" in Italian) to be applied can be avoided in the inside and on the boundary surfaces, and with the rigidity being greater than in the case of a circular cross section. If cracks or hairline cracks in the refractory material are not relevant, it is advantageous to give the cross section a polygonal shape, e.g. triangular, rectangular, square and/or T-shaped (not shown), since these cross-sectional configurations afford better rigidity, in particular less elasticity.

As is shown in FIG. 1(A), the support arm 10 has a circular cross section, but it does not necessarily have to be limited to this.

Arranged on the end areas of each support arm 20 there is a holding or support element 30-1, 30-2, 30-3 for holding or supporting refractory material. The support elements 30 are made in one piece with the corresponding support arm 20 and run essentially perpendicular to the longitudinal axis of the corresponding support arm 20. The support elements 30 are arranged parallel to one another and taper in a direction away from the respective support arm 20. This tapering or narrowing configuration permits easy removal of refractory material secured thereon.

Each support element 30 has a retention arrangement 32 which is provided with a through-bore 34. The retention arrangement 32 has in particular an annular shape, in which case the through-bore 34 is arranged perpendicular to the direction of projection of each support element 30. The retention arrangements 32 prevent the refractory material from easily coming loose from the support elements 30, and yet if easy loosening is required, they can be removed or closed off by means of wax or the like. The retention arrangements 32 can also have a spherical shape (not shown).

Provided on the support arm 20-2 there is a bearing projection or a bearing holder 40 which projects out from the support arm 20-2 in the longitudinal direction thereof and is used for better bearing or holding of the holding device. The bearing projection 40 is used in particular to secure the holding device relative to a negative impression of a dentition during the filling or arrangement of interspaces between the support elements 30 and the negative impression with refractory material.

In one embodiment which is not shown, one or more bearing projections are provided on several support arms.

The distance D between adjacent support arms corresponds to the average distance of adjacent teeth and can vary depending on the application, the distance D being in the range from about 6 to about 14 mm, preferably from about 8 to 12 mm, and most preferably about 9 to 10 mm.

The length L of the support arms 20, measured from about the center of the support elements 30 to the center or center axis of the connection element 22, should be small so that the stability of the support arms 20 is not too greatly reduced and so that the thermal expansion effect, in particular the length expansion, is not too great. The length L is preferably about 10 to 30 mm, preferably about 12 to 20 mm, particularly preferably about 14 to about 16 mm.

The holding device is made of a material which, at high temperatures of up to about 1100° C., does not melt and has a low thermal dilation or expansion. Metal alloys are especially suitable, in particular superalloys, e.g. NIMONIC 105® which has 73.5% Ni, 15% Co, 5% Mo, 4,7% Al, 1.2% Ti and 0.5% Cr. Metal alloys have a coefficient of thermal expansion of approximately $15 \times 10^{-6}$ 1/K and superalloys approximately $10 \times 10^{-6}$ 1/K. It is also advantageous if the material has low surface oxidation, in particular on heat irradiation.

Figure 3C:
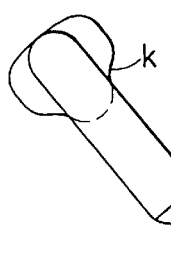
Figure 3D:
Figure 3E:
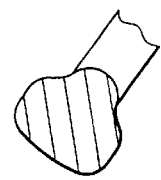
Figure 3F:
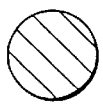
Figure 3B:
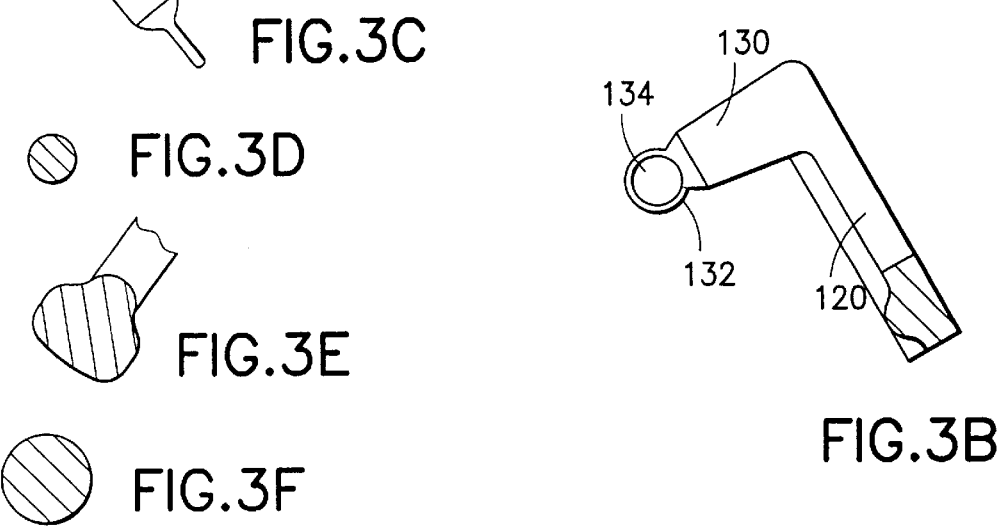

The embodiment of the holding device according to the invention shown in FIG. 3 has six support arms 120-1 to 120-6 which each have a corresponding support element 130-1 to 130-6. The support arms 120 are arranged on a connection element 122 which is of arched design, preferably corresponding to the central arch of the teeth of the upper and/or lower jaw. This holding device is particularly suitable for the manufacture of bridges and/or crowns which cover a larger area of teeth (e.g. a continuous bridge).

According to a further embodiment (not shown), it is also possible for only two support arms or for up to twelve support arms to be provided. The main part 10 or 110 and the connection element 22 or 122 can be one and the same.

An embodiment of the manufacturing process according to the invention is explained hereinbelow with reference to the CAPTEK P® technique. However, the manufacturing process according to the invention can also be used for other techniques, such as the techniques using OPTEK®, CEPLATEC® or CEPLATEC Crown Bridge System® (trade name in Europe, in particular in Italy) or Renaissance® (trade name in USA and Japan) and the like, and in particular when the temperatures used are not in excess of about 1100° C.

a) Forming a negative impression of the dentition or residual dentition, in particular by means of a polyether or silicone impression compound or the like, e.g. of the siloxane or polyvinyl siloxane type, this impression compound drying in about 5 minutes. Alternatively, CAPSIL® can also be used, in which case the hardening time is about 40 minutes.

When forming the negative impression, at least two adjacent teeth are included, as a result of which the distances between the teeth, e.g. prepared bridge abutment teeth, are maintained.

b) Arranging at least two support elements 30-1, 30-2, 30-3; 130-1 to 130-6 of a holding device according to the invention in the sections, in particular the cavities, of the negative impression corresponding to the teeth or tooth gaps. Here, the appropriate holding device is chosen according to the application, in particular on the basis of the number of support elements, the arrangement of the support elements etc. The support elements should preferably be situated approximately in a central section of the cavities of the negative impression, although it is also possible to deviate from this.

During this arrangement, recesses can be formed in the impression compound, namely in accordance with the bearing projection 40 or 140 and the main part 10 or 110 of the holding device in order to fix or secure the holding device, spatially and against tilting, during the subsequent filling step.

c) Filling interspaces between the negative impression and the support elements 30-1, 30-2, 30-3; 130-1 to 130-6 with a filler material consisting of a material which is capable of solidifying, and which in the solidified state is refractory, in particular with a phosphate-bound embedding compound or, for example, with CAPVEST®, in order to form a positive impression of the dentition.

In particular, the CAPVEST® is mixed with a solution of ammonium sulfate diluted with distilled water (e.g. 65%) in order to effect crystallization of the CAPVEST®, in which case the strength of dilution of the CAPVEST® determines the expansion of the refractory material.

d) Curing the filler material, in particular by thermal cycling, e.g. 700° C. for 10 minutes and 1075° C. for 4 minutes. If appropriate, removal of ammonia from the filler material.

d') Applying and/or curing a silicone-type material onto the refractory filler composition, e.g. "CAPTEK® adesivo", in order to facilitate the subsequent application of CAPTEK P®.

d") Securing a wax layer corresponding to a thickness of the final crown which is to be formed.

e) Removing the support elements and the filler material connected thereto, i.e. the positive impression, from the negative impression.

The positive impressions of the teeth or tooth gaps are now secured on the holding device, namely one tooth or gap on one holding element, and the refractory compositions of adjacent teeth or gaps are not in contact. Thus, the expansion capacity of the contiguous areas of refractory material is greatly reduced, since the composition of each contiguous area has been reduced. In addition, the spatial relationships and the orientation between the individual impression areas of the positive impression correspond to those of the areas of the teeth of the patient or the plaster impression.

In the area of the edentulous saddle or seat ("sella edentula" in Italian), projections and/or indents (e.g. an indent in the form of a cross) can be provided on the positive impression, and these can be used for the subsequent arrangement of an intermediate element.

f) Fitting an intermediate element or intermediate member, to be used for the bridge, onto the bridge abutments of the positive impression, in particular by grinding and/or milling. Here, the thickness of the crown can be simulated by wax laminas having a thickness of about 0.4 mm.

g) Securing the intermediate element on the positive impression of an edentulous saddle or seat between the bridge abutments, in particular by means of a hard wax. Here, complementary projections or indents form on the hard wax, and these [missing text] the projections and/or indents formed in step d) in the area of the edentulous saddle (in the above example, a projection in the form of a cross).

h) Forming base layers of the crowns on the positive impressions of the bridge abutments, in particular with a base structure made up of a gold alloy, e.g. CAPTEK P®.

h') Forming receivers for connection elements or bridge anchors of the intermediate element which connects an intermediate element body to the bridge abutment, the receivers at least partially supporting the connection elements from underneath and/or at the sides. The receivers are preferably made of the same material as the base layers of the crowns, e.g. CAPTEK P®.

i) Forming the crowns on the impressions of the bridge abutments, in particular with the intermediate element removed. Thermal cycles are used here in particular.

j) Arranging the intermediate element once again between the crown-fitted positive impressions of the bridge abutments, but without hard wax. The orientation of the intermediate element is now fixed or maintained or positioned by the receivers.

k) Connecting the intermediate element to the crowns, e.g. by means of CAPCON®, CAPTEK G®, CAPFIL®, with CAPCON® first being applied and dried by slightly increasing the temperature, in order to facilitate the subsequent application of CAPTEK G®.

The voids of the base structure (e.g. of CAPTEK P®) are capillarized, i.e. saturated or filled, by means of a gold alloy, e.g. CAPTEK G®. CAPFIL® is also applied in order to compensate the amount of CAPTEK P® and CAPCON®. Thermal cycling is then carried out, as in the preceding steps.

k') Improving or repairing sealing edges of the crowns, in particular fitting the crowns to the master impression made of plaster.

l) Completing the crowns and the bridge, in particular by a ceramic coating, the following steps being carried out in particular:

the crowns and the intermediate element are cleaned in particular with steam at a pressure of about 4 to 5 bar;

a so-called bonder (e.g. CAPBOND® from Leach & Dillon) is applied and thermal treatment or thermal cycling is carried out, e.g. 980° C. for 4 minutes or 990° C. for 2 minutes or 1000° C. for 1 minute;

a matt ceramic is used to fill the intermediate element which is partly hollow;

thermal cycling at a temperature of about 945° C. to 960° C.; and a gloss ceramic is used; etc.

An embodiment of the manufacturing process according to the invention for the manufacture of connected tooth crowns also comprises the following steps:

a) Forming a negative impression of the dentition or residual dentition.

b) Arranging at least two support elements 30-1, 30-2, 30-3; 130-1 to 130-6 of a holding device according to the invention in the sections, in particular cavities, of the negative impression corresponding to the teeth or tooth gaps.

c) Filling interspaces between the negative impression and the support elements 30-1, 30-2, 30-3; 130-1 to 130-6 with a filler material consisting of a material which is capable of solidifying, and which in the solidified state is refractory, in particular with a phosphate-bound embedding compound, in order to form a positive impression of the dentition.

d) Curing the filler material. If appropriate, removal of ammonia from the filler material.

e) Removing the support elements and the filler material connected thereto, i.e. the positive impression, from the negative impression.

f) Forming base layers of the crowns on the positive impressions of the bridge abutments, in particular with a base structure made up of a gold alloy.

g) Forming the crowns on the impressions of the bridge abutments.

h) Connecting the crown, in particular by welding.

i) Completing the crowns and the bridge, in particular by a ceramic coating.

The preceding process steps a) to i) of the manufacturing process for the manufacture of connected tooth crowns can be modified or supplemented in accordance with the process steps of the manufacturing process for the manufacture of bridges.

What is claimed is:

1. A holding device for the manufacture of dental bridges or for connecting adjacent tooth crowns or onlays/inlays, in which said device comprises:
   a main part
   an elongate connection element extending generally transversely in at least one direction from the main part, the connection element being arched along its length such that the arched connection element at least partially corresponds to an arched arrangement of teeth in a jaw;
   at least two support arms which extend unitarily from the connection element,
   each said support arm comprising at least one support element which extends from a location on the respective support arm spaced from the connection element at a predetermined angle from a surface of the support arm adjacent the respective support element.

2. The holding device as claimed in claim 1, in which the support elements each comprise at least one retention arrangement disposed at an end of the support element remote from the support arm and configured for preventing refractory material from coming loose from the holding device.

3. The holding device as claimed in claim 2, in which the retention arrangement has a through-bore of circular shape.

4. The holding device as claimed in claim 2, in which the retention arrangement is substantially spherical.

5. The holding device as claimed in claim 1, in which the support arms are substantially parallel to one another.

6. The holding device as claimed in claim 1, in which two adjacent support elements are spaced apart by a distance which is in the range from about 6 to about 12 mm.

7. The holding device as claimed in claim 1, further comprising a bearing projection formed on at least one of the support arms at a location thereon remote from the connection element and extending away from both the main part and the connection element, whereby the bearing element facilitates bearing of the holding device and enables secure holding of the holding device relative to a negative impression of a dentition during filling of interspaces between the support elements and the negative impression with a refractory material.

8. The holding device as claimed in claim 1, which is made of a metal, whose melting point lies above about 1100° C.

9. The holding device as claimed in claim 1, in which the support arms extend by a length which is in the range from about 10 to 30 mm as measured from about the center of the support element to the center of the connection element.

10. The holding device as claimed in claim 1, in which each said support arm is unitary with the corresponding support element.

11. The holding device as claimed in claim 1, in which the support arms are of non-circular cross-section at least at locations adjacent the respective support elements.

12. The holding device as claimed in claim 11, in which the non-circular cross-section of the support arms has at least two points of reversal of curvature.

13. The holding device as claimed in claim 1, wherein the support elements taper to smaller cross-sectional dimensions at locations spaced further from the respective support arms.

14. The holding device as claimed in claim 13, in which the respective support elements each are of substantially frustoconical shape.

15. A manufacturing process for the manufacture of dental bridges, which process comprises the following steps:
   forming base layers of crowns on the positive impressions of the bridge abutments with a base structure made up of a gold alloy;
   forming the crowns on the impressions of the bridge abutments with the intermediate element removed;
   arranging the intermediate element once again between the crown-fitted positive impressions of the bridge abutments;
   connecting the intermediate element to the crowns;
   completing the crowns and the bridge by a ceramic coating.

16. The manufacturing process as claimed in claim 15, which, after removal step, comprises:
   applying and curing a silicone-type material onto the refractory filler composition and
   securing a wax layer corresponding to a thickness of the final crown which is to be formed on a plaster impression.

17. The manufacturing process as claimed in claim 14, in which the securing step is carried out using a hard wax.

18. The manufacturing process as claimed in claim 17, which, after the step in which the base layer is formed, further comprises forming receivers for connection elements of the intermediate element for connecting an intermediate element body to the bridge abutment, the receivers at least partially supporting the connection elements.

19. The manufacturing process as claimed in claim 18, in which the step for connecting the intermediate element is carried out using a gold alloy for saturating and filling voids by thermal cycling.

20. The manufacturing process as claimed in claim 19, which, after the step of connecting the intermediate element further comprises repairing the sealing edges of the crowns.

21. A manufacturing process for the manufacture of connected tooth crowns or onlays/inlays, which process comprises the following steps:
   forming a negative impression of at least a partial area of the dentition or residual dentition;
   providing a holding device having a main part, an arched connection element extending generally transversely from the main part, a plurality of support arms extending unitarily from the connection element and at least one support element extending at an angle from a location on each said support arm spaced from the respective connection element;
   arranging at least two of the support elements of the holding device in cavities of the negative impression corresponding to the teeth or tooth gaps;
   filling interspaces between the negative impression and the support elements with a filler material consisting of a material which is capable of solidifying, and which in the solidified state is refractory to form a positive impression of the partial area of the dentition;

curing the filler material;

removing the support elements and the filler material connected thereto from the negative impression to define a positive impression;

forming base layers of the crowns on the positive impressions with a base structure made up of a gold alloy;

forming the crowns on the positive impressions;

connecting the crown by welding; and completing the crowns by a ceramic coating.

22. The manufacturing process as claimed in claim 21, in which the curing step comprises a step for removing ammonia from the filler material.

* * * * *